(12) United States Patent
Tanielyan et al.

(10) Patent No.: US 7,030,279 B1
(45) Date of Patent: Apr. 18, 2006

(54) PROCESS FOR TRANSITION METAL FREE CATALYTIC AEROBIC OXIDATION OF ALCOHOLS UNDER MILD CONDITIONS USING STABLE FREE NITROXYL RADICALS

(75) Inventors: Setrak Tanielyan, Maplewood, NY (US); Robert Augustine, Livingston, NJ (US); Oliver Meyer, Muenster (DE); Michael Korell, Denville, NJ (US)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 11/019,257

(22) Filed: Dec. 23, 2004

(51) Int. Cl.
*C07C 45/29* (2006.01)
*C07C 45/38* (2006.01)
*C07C 45/39* (2006.01)

(52) U.S. Cl. .................. 568/322; 568/357; 568/362; 568/403; 568/471

(58) Field of Classification Search ............... None
See application file for complete search history.

(56) References Cited

U.S. PATENT DOCUMENTS

| 5,155,279 | A | * | 10/1992 | Fried | 568/471 |
| 5,155,280 | A | * | 10/1992 | Fried | 568/471 |
| 5,821,374 | A | | 10/1998 | Jenny et al. | 549/263 |
| 6,335,464 | B1 | * | 1/2002 | Ochi et al. | 562/512.2 |
| 6,498,269 | B1 | * | 12/2002 | Merbouh et al. | 562/515 |
| 6,750,371 | B1 | * | 6/2004 | Fritz-Langhals et al. | 568/471 |
| 6,825,384 | B1 | * | 11/2004 | Prakash et al. | 568/402 |

OTHER PUBLICATIONS

Highet, et al., "Solid Manganese Dioxide as an Oxidizing Agent", Am. Chem. Soc. 1955, 77, pp. 4399-4401.

Synth. Org. Chem. Jpn. "Organic Synthesis Using Ruthernium Compounds" 1988, 46, pp. 930-942.
John R. Holum, "Study of the Chromium (VI) Oxide-Pyridine Complex", Org. Chem. 1961, 26, pp. 4814-4816.
Donald G. Lee, et al., "The Aqueous Dichromate Oxidation of Primary Alcohols" J. Org. Chem. 1970, 35, pp. 3589-3590.
Anelli, et al., "Fast and Selective Oxidation of Primary Alcohols to Aldehydes or to Carboxylic Acids and of Secondary Alcohols to Ketones Mediated by Oxoammonium Salts under Two-Phase Conditions", J. Org. Chem., 1987, 52, pp. 2559-2562.
Nooy, et al., "On the Use of Stable Organic Nitroxyl Radicals for the Oxidation of Primary and Secondary Alcohols", Synthesis, 1996, pp. 1153-1174.
Bragd, et al., "TEMPO-mediated Oxidation of Polysaccharides: Survey of Methods and Applications", Catalysis 2004, 27, pp. 49-66.
Sheldon, et al., "Green, Catalytic Oxidations of Alcohols", Acc. Chem. Res. 2002, 35, pp. 774-781.
Kim, et al., "An Efficient Aerobic Oxidation of Alcohols to Aldehydes and Ketones with TEMPO/Ceric Ammonium Nitrate as Catalysts", H.C. Synthesis 2003, 14, pp. 2135-2137.
Gamez, et al., "Cooper (II)-Catalysed Aerobic Oxidation of Primary Alcohols to Aldehydes", Chem. Commun. 2003, 19, pp. 2414-2415.

(Continued)

*Primary Examiner*—Sikarl A. Witherspoon
(74) *Attorney, Agent, or Firm*—Oblon, Spivak, McClelland, Maier & Neustadt, P.C.

(57) ABSTRACT

An alcohol can be oxidized by a process in which a primary or secondary alcohol are reacted with an oxygen-containing gas in the presence of a catalyst composition containing (i) a stable free nitroxyl radical derivative, (ii) a nitrate source, (iii) a bromide source, and (iiii) a carboxylic acid, thereby obtaining an aldehyde or a ketone.

30 Claims, 2 Drawing Sheets

OTHER PUBLICATIONS

Inokuchi, et al., "One-Pot Conversion of Primary Alcohols to alpha-Oxygenated Alkanals with Tempo in Combination with Molecular Oxygen and Ruthenium Complex", Tetrahedron Letters 1995, 36, pp. 3223-3226.

Dijksmann, et al. "Efficient and Selective Aerobic Oxidation of Alcohols Into Aldehydes and Ketones Using Ruthenium/TEMPO as the Catalytic System", J. Am. Chem. Soc 2001, 123, pp. 6826-6833.

Cecchetto, et al., "Efficient Mn-Cu and Mn-Co-TEMPO-Catalysed Oxidation of Alcohols into Aldehydes and Ketones by Oxygen under Mild Conditions", Tetrahedron Letts 2001, 42, pp. 6651-6653.

Liu, et al., "Transition-Metal-Free: A Highly Efficient Catalytic Aerobic Alcohol Oxidation Process", J. Am. Chem. Soc. 2004, 126, pp. 4112-4113.

Imtiaz, et al., TEMPO-Catalyzed Aerobic Oxidation of Alcohols to Aldehydes and Ketones in Ionic Liquid [bmin][$PF_6$].

* cited by examiner

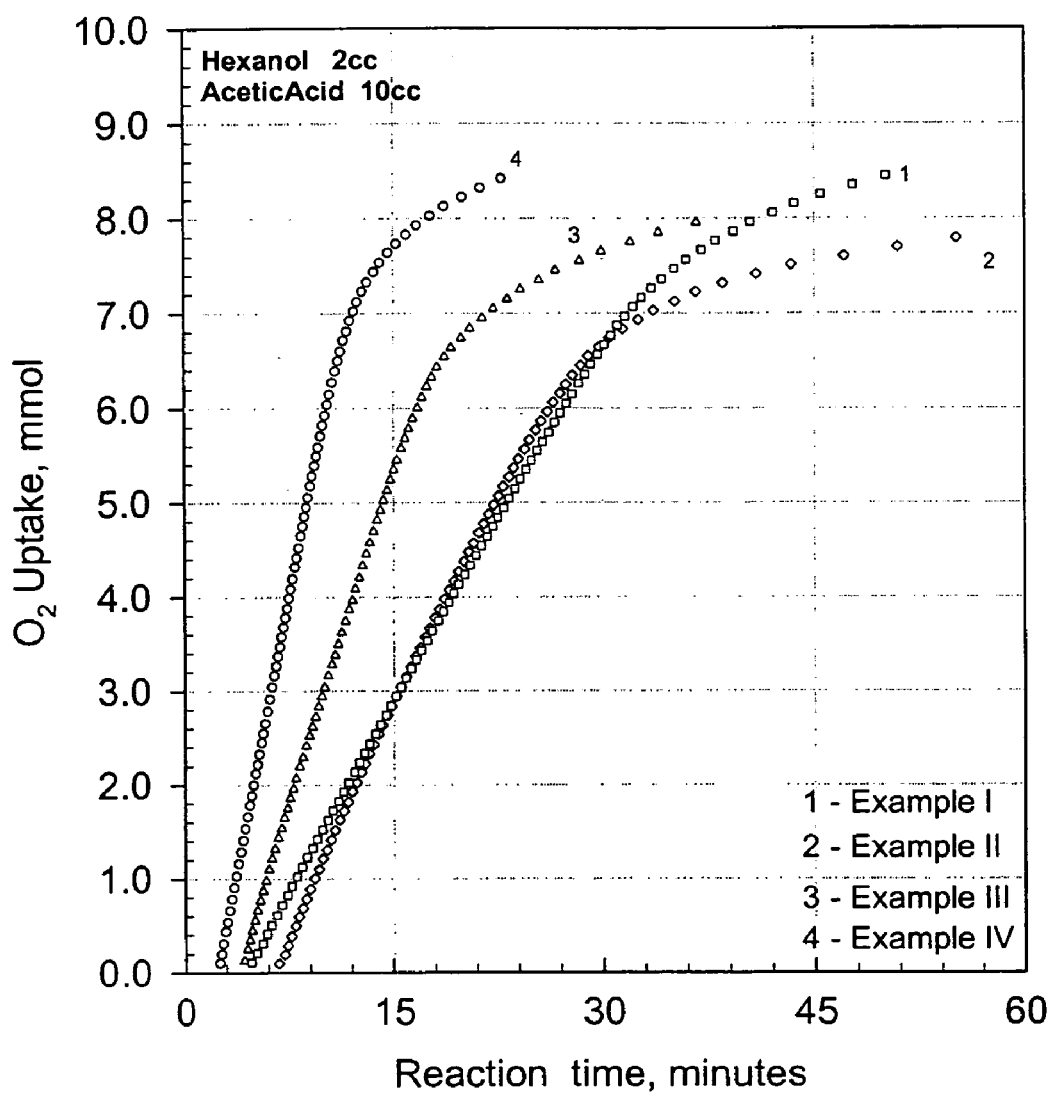
Figure 1. Liquid Phase Oxydation of Hexanol-1
TEMPO based system catalyst compositions
Hexanol-16mmol, Temperature 46C, 15psi

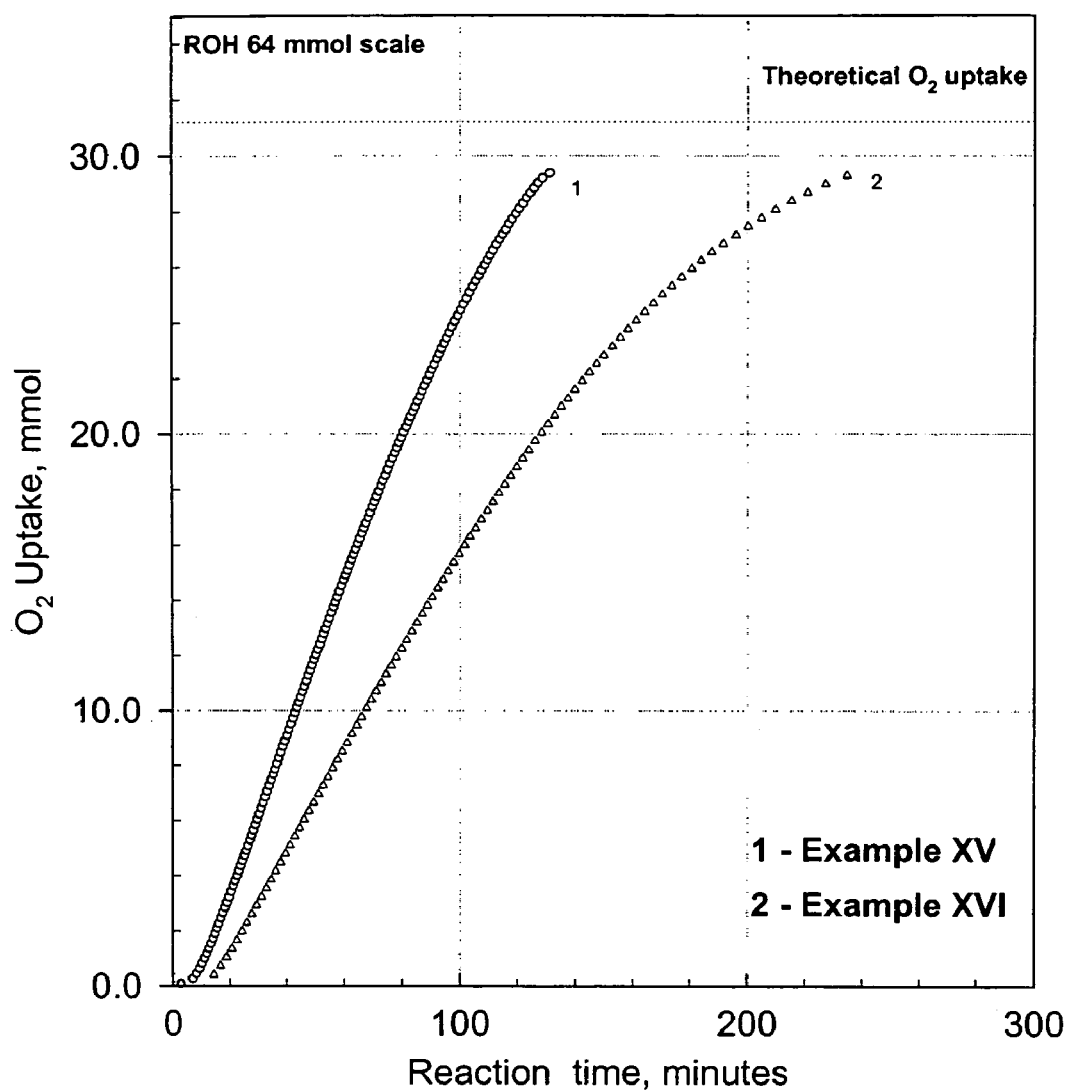
Figure 2. Liquid Phase Oxidation of 1-Hexanol
AA-TEMPO = 0.48mmol, NBS = 0.55mmol, $Mg(NO_3)_2$ = 0.48 mmol
ROH = 8cc (64mmol), Acetic acid 4 ml, Temperature 48 $^0$C
1 - Example XV
2 - Example XVI

PROCESS FOR TRANSITION METAL FREE CATALYTIC AEROBIC OXIDATION OF ALCOHOLS UNDER MILD CONDITIONS USING STABLE FREE NITROXYL RADICALS

BACKGROUND OF THE INVENTION

1. Field of the Invention

The present invention relates to a transition-metal-free aerobic oxidation method for primary and secondary alcohols towards the corresponding aldehydes and ketones at low pressures in the presence of a stable free nitroxyl radical.

2. Discussion of the Background

The oxidation of alcohols to the corresponding aldehydes, ketones or acids certainly represents one of the most important functional group transformations in organic synthesis and there are numerous methods reported in the literature (Sheldon, R. A., Kochi, J. K. *Metal-Catalysed Oxidations of Organic Compounds*; Academic Press: New York, 1981; Hudlicky, M. *Oxidations in Organic Chemistry*; American Chemical Society: Washington D.C. 1990).

However, relatively few methods describe the selective oxidation of primary or secondary alcohols to the corresponding aldehydes and ketones and most of them traditionally use a stoichiometric terminal oxidant such as chromium oxide (Holum, J. R. J. Org. Chem. 1961, 26, 4814–4816), dichromate (Lee, D. G; Spitzer, U. A. J. Org. Chem. 1970, 35, 3589–3590), manganese oxide (Highet, R. J.; Wildman, W. C. J. Am. Chem. Soc. 1955, 77, 4399–4401) and osmium or ruthenium as primary oxidants (Murahashi, S.-I; Naota, T. J. Synth. Org. Chem. Jpn. 1988, 46, 930–942).

A convenient procedure for the oxidation of primary and secondary alcohols is reported by Anelli and co-workers (J. Org. Chem., 1987, 52, 2559). Accordingly, the oxidation has been carried out in $CH_2Cl_2$—aqueous buffer of pH 8.5–9.5 utilizing 2,2,6,6-tetramethylpiperidine-1-oxyl (TEMPO) as a catalyst and KBr as a co-catalyst. The terminal oxidant in this system is NaOCl. A major disadvantage of using sodium hypochlorite or any other hypohalite as stoichiometric oxidant is that per mol of alcohol oxidized during the reaction one mole of halogenated salt is formed. Furthermore, the use of hypohalites very frequently leads to the formation of undesirable halogenated by-products thus necessitating further purification of the oxidation product. Extensive review of methods based on the TEMPO based oxidations is found elsewhere (Synthesis, 1996, 1153–1174; Topics in Catalysis 2004, 27, 49–66; Acc. Chem. Res. 2002, 35, 774–781).

U.S. Pat. No. 5,821,374 discloses the use of N-chloro compounds such as N-chloro-4-toluenesulfonamide sodium salt as an oxidant in the TEMPO catalyzed oxidation of primary alcohols to aldehydes. The major drawback of this method is the use of large amounts of solvents and the toxicity of the N-chlorinated aromatics used as oxidants.

In recent years, a lot of efforts have been spent on developing both selective and environmentally friendly oxidation methods using either air or oxygen as primary oxidants and catalyst systems, based on stable nitroxyl radicals as catalysts and transition metal salts as co-catalysts. The most commonly used co-catalysts are $(NH_4)_2Ce(NO_3)_6$ (Kim, S. S.; Jung, H. C. Synthesis 2003, 14, 2135–2137), $CuBr_2$-2,2'-bipyridine complex (Gamez, P; Arends, I. W. C. E.; Reedijk, J.; Sheldon, R. A. Chem. Commun. 2003, 19, 2414–2415), $RuCl_2(PPh_3)_3$ (Inokuchi, T.; Nakagawa, K.; Torii, S. Tetrahedron Letters 1995, 36, 3223–3226 and Dijksman, A.; Marino-Gonzalez, A.; Payeras, A. M.; Arends, I. W. C. E.; Sheldon, R. A. J. Am. Chem. Soc. 2001, 123, 6826–6833), $Mn(NO_3)_2$—$Co(NO_3)_2$ and $Mn(NO_3)_2$—$Cu(NO_3)_2$ (Cecchetto, A.; Fontana, F.; Minisci, F.; Recupero, F. Tetrahedron Letters 2001, 42, 6651–6653), and CuCl in ionic liquid [bmim][$PF_6$] (Imtiaz, A. A; Gree, R. Organic Letters 2002, 4, 1507–1509).

However, from an economic and environmental point of view the above mentioned oxidation methods suffer from one major drawback. They depend on substantial amounts of expensive and/or toxic transition metal complexes and some of them require the use of halogenated solvents such as dichloromethane, which makes them unsuitable for industrial scale production. Very recently, Hu et al. disclosed a process for aerobic oxidation of primary and secondary alcohols utilizing a TEMPO based catalyst system, free of any transition metal co-catalyst (Liu, R.; Liang, X.; Dong, C.; Hu, X. J. Am. Chem. Soc. 2004, 126, 4112–4113). In this process, the authors employed a mixture of TEMPO (1 mol %), sodium nitrite (4–8 mol %) and bromine (4 mol %) as the active catalyst system. The oxidation takes place at temperatures between 80–100° C. and at an air pressure of 4 bar. However, this process is only successful with activated alcohols. If benzyl alcohol is used, quantitative conversion is achieved after 1–2 h of reaction time. In the case of non-activated aliphatic alcohols (such as 1-octanol) or cyclic alcohols (such as cyclohexanol) the air pressure needs to be raised up to 9 bar and 3 to 4 h of reaction time were necessary to reach complete conversion. Disadvantageously, this new oxidation procedure again depends on dichloromethane as a solvent, which is a major obstacle for an industrial application of the method. Furthermore, elemental bromine as a co-catalyst is rather difficult to handle on a technical scale due to its high vapor pressure, toxicity and severe corrosion when applied in standard steel apparatus. Other disadvantages of this method are the rather low substrate concentration in the solvent used and the observed formation of bromination by-products.

SUMMARY OF THE INVENTION

It is therefore an object of the present invention to provide a process for the catalytical oxidation of alcohols to the corresponding aldehydes and ketones under mild conditions with high selectivity, high reaction rates and high yields by using an oxygen-containing gas as "clean" oxidant in combination with an environmentally friendly and easy to handle catalyst system.

It is another object of the present invention to provide a process which overcomes the disadvantages involved in the oxidation procedures mentioned above by not comprising any transition metal catalyst, hazardous co-catalyst or halogenated solvent.

It is a further object of the present invention to provide an oxidation process which is easily and safely transferable into technical scale.

This and other objects have been achieved by the present invention the first embodiment of which includes a process for oxidation of an alcohol, comprising:

reacting a primary or secondary alcohol with an oxygen-containing gas in the presence of a catalyst composition comprising
(i) a stable free nitroxyl radical derivative,
(ii) a nitrate source,
(iii) a bromide source, and
(iiii) a carboxylic acid;
thereby obtaining an aldehyde or a ketone.

BRIEF DESCRIPTION OF DRAWINGS

FIG. 1 shows the reaction time dependence of the oxygen uptake in the liquid phase oxidation of hexanol-1 (Examples I–IV).

FIG. 2 shows the reaction time dependence of the oxygen uptake in the liquid phase oxidation of hexanol-1 (Examples XV–XVI).

DETAILED DESCRIPTION OF THE INVENTION

It has surprisingly been found by the inventors of the present invention that, even in the absence of any transition metal catalyst or any halogenated solvent, alcohols can be oxidized selectively in the presence of an oxygen-containing gas at low pressure and mild conditions by using a stable free nitroxyl radical, a nitrate source, a bromide source and a carboxylic acid as the catalytic active system. The described process represents a highly cost effective catalytic oxidation method that can easily and safely be scaled up and transferred into technical scale.

In the context of the present invention, a "stable free nitroxyl radical" is a free nitroxyl radical which is substantially stable at room temperature during storage for a minimum period of one week in the presence of oxygen. Preferably a "stable free nitroxyl radical" is a free nitroxyl radical which is not substituted by a hydrogen atom at any α-C-atom next to the nitrogen atom. Further, the "stable free nitroxyl radical" preferably retains a content of at least 90% of the free nitroxyl radical after storage for one week at 25° C. in the presence of oxygen, based on the initial content of free nitroxyl radical.

The present invention relates to a transition metal free catalytic process for oxidation of alcohols into the corresponding aldehydes or ketones. In one embodiment, the process of the present invention which comprises reacting an alcohol with an oxygen-containing gas, a stable free nitroxyl radical having the general formula (I) or its derivative having formula (II), a nitrate source, a bromide source and a carboxylic acid at an oxygen partial pressure of 0.1–10 bar and at a temperature between 0–100° C. The oxygen partial pressure includes all values and subvalues therebetween, especially including 0.5, 1, 1.5, 2, 2.5, 3, 3.5, 4, 4.5, 5, 5.5, 6, 6.5, 7, 7.5, 8, 8.5, 9 and 9.5 bar. The temperature includes all values and subvalues therebetween, especially including 5, 10, 15, 20, 25, 30, 35, 40, 45, 50, 55, 60, 65, 70, 75, 80, 85, 90 and 95° C.

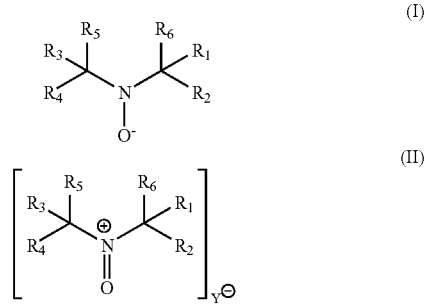

In formulae (I) and (II), $R^1$, $R^2$, $R^3$, $R^4$, $R^5$, and $R^6$ are simultaneously or independently of each other $(C_1–C_{10})$-alkyl, $(C_1–C_{10})$-alkenyl, $(C_1–C_{10})$-alkoxy, $(C_6–C_{18})$-aryl, $(C_7–C_{19})$-aralkyl, $(C_6–C_{18})$-aryl-$(C_1–C_8)$-alkyl or $(C_3–C_{18})$-heteroaryl;

$R^5$ and $R^6$ can also be bonded together via a $(C_1–C_4)$-alkyl chain, which can be saturated or unsaturated, unsubstituted or substituted by one or more $R^1$, $C_1–C_8$-amido, halogen, oxy, hydroxyl, amino, alkylamino, dialkylamino, arylamino, diarylamino, alkylcarbonyloxy, arylcarbonyloxy, alkylcarbonylamino or arylcarbonylamino. In formula (II) $Y^-$ group is an anion.

The compounds of formulae (I) or (II) may be used alone or in mixtures.

The process of the present invention can be applied for primary as well as for secondary alcohols. According to their reactivity, primary alcohols are oxidized much faster than secondary ones. Primary alcoholic functions can be oxidized selectively in the presence of secondary alcoholic groups within the same molecule. However, the alcohol used in the process of the present invention preferably comprises a primary alcoholic function.

The term "alcohols" as used in the present invention includes organic compounds having primary or secondary hydroxyl groups. The term "lower alcohol" as used herein means an alcohol having 1 to 10 carbon atoms and the term "higher alcohol" as used herein means an alcohol having 11 or more carbon atoms. Examples include alcohols such as methanol, ethanol, propyl alcohol, butyl alcohol, pentanol, 2-methyl-1-butanol, 3-methyl-1-butanol, neopentyl alcohol, hexanol, 2-methyl-1-pentanol, neohexyl alcohol, heptanol, octanol, 2-ethyl-1-hexanol, nonyl alcohol, decyl alcohol, lauryl alcohol, dodecyl alcohol, eicosyl alcohol. Examples of unsaturated alcohols include allyl alcohol, crotyl alcohol and propargyl alcohol. Examples of aromatic alcohols include benzyl alcohol, phenyl ethanol, phenyl propanol and the like. The alcohol may be a single alcohol or a mixture of alcohols.

The stable free nitroxyl radical may be of the general formula (I) or its derivative (II) in which $R^1$, $R^2$, $R^3$, $R^4$, $R^5$, and $R^6$ are simultaneously or independently of each other $(C_1–C_{10})$-alkyl, $(C_1–C_{10})$-alkenyl, $(C_1–C_{10})$-alkoxy, $(C_6–C_{18})$-aryl, $(C_7–C_{19})$-aralkyl, $(C_6–C_{18})$-aryl-$(C_1–C_8)$-alkyl or $(C_3–C_{18})$-heteroaryl; $R^5$ and $R^6$ can also be bonded together via a $(C_1–C_4)$-alkyl chain, which can be saturated or unsaturated, unsubstituted or substituted by one or more $R^1$, $C_1–C_8$-amido, halogen, oxy, hydroxyl, amino, alkylamino, dialkylamino, arylamino, diarylamino, alkylcarbonyloxy, arylcarbonyloxy, alkylcarbonylamino or arylcarbonylamino. In formula (II) the $Y^-$ group is an anion.

Examples of stable free nitroxyl radicals or their oxoammonium derivatives include 2,2,6,6,-tetramethylpiperidine-1-oxyl (TEMPO) and its 4-substituted derivatives such as 4-methoxy-2,2,6,6-tetramethylpiperidine-1-oxyl (4-MeO-TEMPO), 4-oxo-2,2,6,6-tetramethylpiperidine-1-oxyl (4-oxo-TEMPO), 4-hydroxy-2,2,6,6-tetramethylpiperidine-1-oxyl (4-hydroxy-TEMPO), 4-benzoyloxy-2,2,6,6-tetramethylpiperidine-1-oxyl (BnO-TEMPO), 4-acetamino-2,2,6,6-tetramethylpiperidine-1-oxyl (AA-TEMPO), 4-amino-2.2,6,6-tetramethylpiperidine-1-oxyl. 4-acetamido-2.2,6,6-tetramethylpiperidine-1-oxyl, N,N-dimethylamino-2,2,6,6-tetramethyl-piperidine-1-oxyl (NNDMA-TEMPO), 3,6-dihydro-2,2,6,6-tetramethyl-1 (2H)-pyridinyl-oxy (DH-TEMPO), and bis-(2,2,6,6-tetramethyl-piperidine-1-oxyl-4-yl) sebacate. The stable free nitroxyl radicals may be used alone or in mixtures.

The tetramethylpiperidine-N-oxyl structure of formulae (I) or (II) or mixtures thereof can also be a substituent of a larger macromolecule, an oligomeric or even a polymeric structure. An example of an oligomeric structure is shown below.

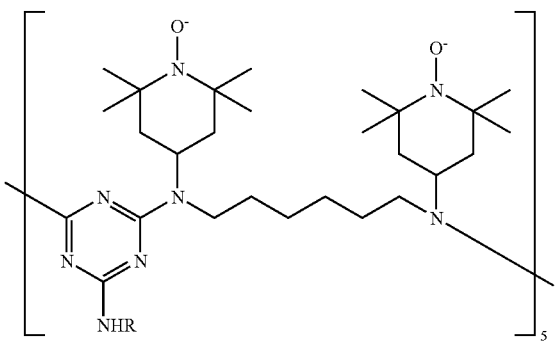

The "heterogenized" forms of the stable free nitroxyl radicals or their oxoammonium derivatives can also be used. This means that the nitroxyl radicals or their oxoammonium derivatives are supported on, for example, a solid support. A solid support can be an inorganic support, such as aluminum oxide, silica, titanium oxide; or zirconium oxide; or polymers; composites; or carbon materials.

The ratio of stable free nitroxyl radical to alcohol substrate is not particularly limited. Preferably, this ratio is kept as low as possible for economic and ecological reasons. The stable free nitroxyl radical derivative may be present in an amount of from about 0.001–10 mol %, based on the amount of said alcohol. Preferably, the catalytic amount of nitroxyl radical is 0.01–2 mol %, and most preferably 0.5–1 mol %, with respect to the substrate alcohol. The amount of stable free nitroxyl radical includes all values and subvalues therebetween, especially including 0.005, 0.01, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, and 9.5 mol %.

The nitrate source may be nitric acid, ammonium nitrate, alkyl ammonium nitrate or any alkali or alkaline-earth nitrate, preferably magnesium nitrate. Magnesium nitrate has the advantage to be soluble, non-toxic, cheap and easily available. A single nitrate source or a mixture of sources may be used. Since the nitrate source present in the process of present invention serves as a co-catalyst, only catalytic amounts are necessary. Preferably, the amount of nitrate source may be 0.01–10 mol %, more preferably 0.1–2 mol %, and most preferably 0.5–1 mol % with respect to the substrate alcohol. The amount of nitrate anion includes all values and subvalues therebetween, especially including 0, 0.5, 0.1, 0.5, 1, 1.5, 2, 2.5, 3, 3.5, 4, 4.5, 5, 5.5, 6, 6.5, 7, 7.5, 8, 8.5, 9 and 9.5 mol %.

The bromide source may be any N-brominated species, such as N-bromosuccinimide, N-bromophthalimide, tetrabutyl ammonium bromide; or an inorganic salt such as $NH_4Br$ or any other alkali bromide or alkaline-earth bromide, preferably N-bromosuccinimide. A single bromide source or a mixture of bromide sources may be used. The N-bromosuccinimide has the advantage to be readily available, non-corrosive, non-toxic and easy to handle. Since the bromide source present in the process of present invention serves as a co-catalyst, only catalytic amounts are necessary. Preferably, the amount of bromide source may be 0.01–10 mol %, preferably 0.1–2 mol %, and most preferably 0.5–1 mol % with respect to the substrate alcohol. The amount of bromide source includes all values and subvalues therebetween, especially including 0, 0.5, 0.1, 0.5, 1, 1.5, 2, 2.5, 3, 3.5, 4, 4.5, 5, 5.5, 6, 6.5, 7, 7.5, 8, 8.5, 9 and 9.5 mol %.

The carboxylic acid may be acetic acid, propionic acid or any other carboxylic acid that forms a homogeneous reaction mixture. Preferably, the organic acid is acetic acid. The carboxylic acid may be used alone, in mixtures or in combination with other solvents. Additional solvent to suspend the reactants in the process of the present invention may be used or omitted. The solvent may be present in an amount of from 0 vol. % to about 70 vol. % based on the volume of the substrate alcohol used. The amount of solvent includes all values and subvalues therebetween, especially including 5, 10, 15, 20, 25, 30, 35, 40, 45, 50, 55, 60, and 65 vol. %.

A preferred solvent, if needed, is acetonitrile, tetrahydrofuran, ethyl acetate, acetone, diethyl ether, methyl tert-butyl ether and the like, or a mixture of those solvents. Preferably, the amount of carboxylic acid is 0.1–200 mol %, and most preferably 10–50 mol % with respect to the substrate alcohol. The amount of carboxylic acid includes all values and subvalues therebetween, especially including 0.5, 1, 5, 10, 20, 40, 60, 80, 100, 120, 140, 160 and 180 mol %.

To optimize the space-time-yield the process of the present invention is preferably conducted without any additional solvent. Preferably, the carboxylic acid is not only used as an additive but might be necessary as a solvent to keep the reaction mixture homogenous. However, the amount of carboxylic acid is kept as low as possible due to economical reasons.

As the oxygen containing gas, pure oxygen, any make up mixture of oxygen and an inert gas or more preferably air may be employed. The oxygen partial pressure may be selected depending on the alcohol substrate but is not particularly limited. However, the reaction rate does increase markedly with increasing the oxygen partial pressure. The oxygen partial pressure in general is maintained in the range of 0.1–70 bar, preferably in the range of 0.1–10 bar, most preferably in the range of 0.5–2 bar. The oxygen partial pressure includes all values and subvalues therebetween, especially including 0.5, 1, 5, 10, 15, 20, 25, 30, 35, 40, 45, 50, 55, 60 and 65 bar. The process preferably proceeds at an oxygen partial pressure of from 0.1 to 10 bar.

When pure oxygen is used, the reaction pressure is in the range 0.2–5 bar, preferably 0.5–1 bar. The reaction pressure using oxygen includes all values and subvalues therebetween, especially including 0.5, 1, 1.5, 2, 2.5, 3, 3.5, 4 and 4.5 bar. Using air, the reaction pressure is in the range of 1–10 bar, preferably 2–5 bar. The reaction pressure using air includes all values and subvalues therebetween, especially including 1.5, 2, 2.5, 3, 3.5, 4, 4.5, 5, 5.5, 6, 6.5, 7, 7.5, 8, 8.5, 9, and 9.5 bar.

The reaction temperature at which the process of the present invention is carried out depends on the reactivity of the alcohol substrate and is in general between 0° C. and 100° C., preferably between 20° C. to 80° C., most preferably between 40° C. to 60° C. The reaction temperature includes all values and subvalues therebetween, especially including 10, 20, 30, 40, 50, 60, 70, 80 and 90° C.

The process of the present invention can be run as a batch, a semi-batch or as a continuous process. Furthermore, it is not limited to a certain reactor type or setup. Thus, stirred tank reactors, tube reactors, reactor cascades, micro reactors or any possible combination of those reactor types might be used.

The oxidation product can be worked up by any known methods, such as by phase-splitting with addition of water and distillation of the organic phase. Depending on the requirements for purity, any other chemical methods can also be used.

The process of the present invention can be carried out in a variety of ways. For example, the required amounts of nitrate source (e.g. $Mg(NO_3)_2 \cdot 6H_2O$), bromide source (e.g. N-bromosuccinimide (NBS)), stable free nitroxyl radical (for example TEMPO or AA-TEMPO) and the carboxylic acid (e.g. acetic acid) are charged into the reaction flask which is then connected to a volumetric manifold. The catalyst solution is stirred until the solid components are completely dissolved and is purged twice with oxygen or air. The stirring may take 30 sec. to 10 min. preferably 5 min. The mixture is then heated to the target temperature and the flask is pressurized to the desired value either using oxygen or air. To initiate the reaction, the required amount of alcohol is injected into the reaction flask through a septum adapter using a gas tight syringe. The oxygen uptake is continuously monitored and recorded against the time. After completion of the reaction, the product solution is analyzed by GC or GC/MS using decane as an internal standard.

The alcohol can also be injected in form of a solution in carboxylic acid. The oxygen-containing gas can also be introduced after combining all the other reaction components. It is also possible to combine all reaction components with exception of the stable free nitroxyl radical derivative and to start the reaction by introduction of the stable free nitroxyl radical derivative. The various modes of operability and the robustness of the process are great advantages.

Following the reaction, the product can be worked up by known methods. An expedient method is first a phase split of the reaction product by addition of water or saturated salt solution, followed by extraction of the aqueous phase with suitable solvent. Suitable solvents for the extraction step are selected from the group of solvents such as methylene chloride, ethyl acetate, butyl acetate, di-tert-butyl ether, methyl tert-butyl ether; or saturated hydrocarbon solvents such as pentane or hexane. The desired aldehyde or ketone can be recovered from the combined organic phase using traditional methods of distillation, fractional distillation, crystallization or the aldehyde can be further purified via reaction with sodium metabisulphite ($Na_2S_2O_5$).

In conclusion, an efficient and environmentally benign process for aerobic oxidation of alcohol has been developed. According to the new procedure, either molecular oxygen or air can be used as terminal oxidant. The catalyst system is comprised of a stable free nitroxyl radical, a nitrate, a bromide source and a carboxylic acid. High reaction rates and high aldehyde selectivity can be achieved even at high initial concentration of alcohol in the range, where most of the known catalyst compositions are completely inhibited. Another advantage of the method of the present invention is that the primary hydroxyl groups may be oxidized selectively in the presence of secondary ones. The method has the additional advantage that it does not require the use of chlorinated solvents and the product aldehyde is free of any halogenated by-products.

Having generally described this invention, a further understanding can be obtained by reference to certain specific examples which are provided herein for purposes of illustration only, and are not intended to be limiting unless otherwise specified.

EXAMPLES

Example I

Examples I–IV represent the activity of some TEMPO derivatives used in the catalyst composition of the present invention for the selective oxidation of hexanol-1 to hexanal. The examples I–IV were carried out for illustrative purposes at relatively low loading of the substrate alcohol in the starting reaction solution. A graphical presentation of the oxidation reactions is given in FIG. 1.

0.0913 g 4-MeO-TEMPO (0.48 mmol), 0.124 g of $Mg(NO_3)_2 \cdot 6H_2O$ (0.48 mmol) and 0.0086 g N-bromosuccinimide (0.048 mmol) were dissolved in 10 ml of glacial acetic acid and the resulting solution was charged into a 75 ml reaction flask. The flask was sealed and attached to the gas delivering volumetric unit. The catalyst solution was purged with oxygen at least three times and then heated to 46° C. while stirring. When the temperature reached the target value, 2 ml of hexanol-1 (16 mmol) were dosed in using a gas tight syringe. The flask was then pressurized with oxygen to 1 bar (15 psi), the stirring rate was set to 1200 rpm and the progress of the oxidation was followed by the oxygen uptake, which was continuously monitored and recorded against the time. After the reaction was completed, an aliquot was analyzed by GC using decane as an internal standard. The recorded oxygen uptake rate as calculated from curve 1 in FIG. 1 is 0.263 mmol $O_2$/min and the GC analysis of the reaction solution showed alcohol conversion of 99.4% at 93.1% selectivity to hexanal.

Example II

Example II represents the activity of TEMPO derivative as a component of the catalyst composition—curve 2 in FIG. 1.

0.0766 g TEMPO (0.48 mmol), 0.124 g of $Mg(NO_3)_2 \cdot 6H_2O$ (0.48 mmol) and 0.013 g N-bromosuccinimide (0.072 mmol) were dissolved in 10 ml of glacial acetic acid and the resulting solution was charged into a 75 ml reaction flask. The flask was sealed and attached to the gas delivering volumetric unit. The catalyst solution was purged with oxygen at least three times and then heated to 46° C. while stirring. When the temperature reached the target value, 2 ml of hexanol-1 (16 mmol) were dosed in using a gas tight syringe. The flask was then pressurized with oxygen to 1 bar (15 psi), the stirring rate was set to 1200 rpm and the progress of the oxidation was followed by the oxygen uptake, which was continuously monitored and recorded against the time. The recorded oxygen uptake rate was 0.332 mmol $O_2$/min and the GC analysis after 60 min reaction time showed 96.0% conversion of the starting alcohol and 96.2% selectivity to hexanal —FIG. 1, curve 2.

Example III

Example III represents the activity of 4-hydroxy-TEMPO derivative as a component of the catalyst composition—curve 3 in FIG. 1.

0.169 g 4-hydroxy-TEMPO (0.96 mmol), 0.311 g of $Mg(NO_3)_2 \cdot 6H_2O$ (1.2 mmol) and 0.0086 g N-bromosuccinimide (0.048 mmol) were dissolved in 10 ml of glacial acetic acid and the resulting solution was charged into a 75 ml reaction flask. The flask was sealed and attached to the gas delivering volumetric unit. The catalyst solution was purged with oxygen at least three times and then heated to 46° C. while stirring. When the temperature reached the target value, 2 ml of hexanol-1 (16 mmol) were dosed in using a gas tight syringe. The flask was then pressurized with oxygen to 1 bar (15 psi), the stirring rate was set to 1200 rpm and the progress of the oxidation was followed by the oxygen uptake, which was continuously monitored and recorded against the time. The recorded oxygen uptake rate was 0.467 mmol $O_2$/min and the GC analysis after 45 min reaction time showed 98.0% conversion of the starting alcohol and 93.8% selectivity to hexanal —FIG. 1, curve 3.

Example IV

Example IV represents the activity of 4-acetamido-TEMPO (AA-TEMPO) derivative as a component of the catalyst composition—curve 4 in FIG. 1.

0.1394 g AA-TEMPO (0.64 mmol), 0.311 g of $Mg(NO_3)_2 \cdot 6H_2O$ (1.2 mmol) and 0.0086 g N-bromosuccinimide (0.048 mmol) were dissolved in 10 ml of glacial acetic acid and the resulting solution was charged into a 75 ml reaction flask. The flask was sealed and attached to the gas delivering volumetric unit. The catalyst solution was purged with oxygen at least three times and then heated to 46° C. while stirring. When the temperature reached the target value, 2 ml of hexanol-1 (16 mmol) were dosed in using a gas tight syringe. The flask was then pressurized with oxygen to 1 bar (15 psi), the stirring rate was set to 1200 rpm and the progress of the oxidation was followed by the oxygen uptake, which was continuously monitored and recorded against the time. The recorded oxygen uptake rate was 0.768 mmol $O_2$/min and the GC analysis after 20 min reaction time showed 100.0% conversion of the starting alcohol and 94.78% selectivity to hexanal —FIG. 1, curve 4.

Examples V–XI represent the application of the present invention to the selective oxidation of different alcohols carried out at high loading of the substrate alcohol in the starting reaction solution.

Example V 0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The flask was sealed and attached to the gas delivering volumetric unit. The catalyst solution was purged with oxygen at least three times and then heated to 46° C. while stirring. When the temperature reached the target value, the required amount of the hexanol-1 (64 mmol) was injected into the reactor, using a gas tight syringe. The flask was then pressurized with oxygen to 1 bar (15 psi), the stirring rate was set to 1200 rpm. The recorded oxygen uptake rate as calculated from the oxygen uptake curve was 0.211 mmol $O_2$/min and the GC analysis of the reaction solution after 280 min showed alcohol conversion of 98% at 94% selectivity to hexanal.

Example VI

Example VI Represents the Oxidation of Hexanol-2

0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid, and the resulting solution was charged into the reaction flask. The amount of hexanol-2, the temperature, the pressure and the stirring rate were the same as for Example V. The recorded oxygen uptake rate was 0.024 mmol $O_2$/min and the GC analysis after 600 min reaction time showed 34% conversion of the starting alcohol and 96% selectivity to hexanon-2.

Example VII

The Example Represents the Oxidation of Heptanol-1

0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The amount of heptanol-1, the temperature, the pressure and the stirring rate were the same as for Example V. The recorded oxygen uptake rate was 0.181 mmol $O_2$/min and the GC analysis after 400 min reaction time showed 100% conversion of the starting alcohol and 99% selectivity to heptanal.

Example VIII

The Example Represents the Oxidation of Octanol-1

0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The amount of octanol-1, the temperature, the pressure and the stirring rate were the same as for Example V. The recorded oxygen uptake rate was 0.168 mmol $O_2$/min and the GC analysis after 400 min reaction time showed 100% conversion of the starting alcohol and 99% selectivity to octanal.

Example IX

The Example Represents the Oxidation of Dodecanol-1

0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The amount of dodecanol-1, the temperature, the pressure and the stirring rate were the same as for Example V. The recorded oxygen uptake rate was 0.122 Mmol $O_2$/min and the GC analysis after 400 min reaction time showed 93% conversion of the starting alcohol and 89% selectivity to dodecanal.

Example X

The Example Represents the Oxidation of Benzyl Alcohol 0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The amount of benzyl alcohol, the temperature, the pressure and the stirring rate were the same as for Example V. The recorded oxygen uptake rate was 0.631 mmol $O_2$/min and the GC analysis after 60 min reaction time showed 100% conversion of the starting alcohol and 93% selectivity to benzyl aldehyde.

Example XI

The Example Represents the Oxidation of 1-phenylethanol 0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The amount of 1-phenylethanol, the temperature, the pressure and the stirring rate were the same as for Example V. The recorded oxygen uptake rate was 0.248 mmol $O_2$/min and the GC analysis after 240 min reaction time showed 89% conversion of the starting alcohol and 100% selectivity to acetophenone.

The following Examples XII–XVI represent the different modes of preparing the catalyst composition, the introduction of the hexanol-1 substrate and the exposure to oxygen.

Example XII

The example is similar to V but the catalyst composition was heated in argon, the oxygen was admitted next followed by injection of hexanol-1.

0.1045 g AA-TEMPO (0.48 mmol), 0.124 of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The flask was sealed and attached to the gas delivering volumetric unit. The catalyst solution was purged with argon at least three times and then heated to 46° C. while stirring. When the temperature reached the target value, the argon was replaced for oxygen and after two minutes equilibration time, 8 ml hexanol-1 (64 mmol) were injected using a gas tight syringe. The recorded oxygen uptake rate was 0.221 mmol $O_2$/min and the GC analysis of the reaction solution after 200 min showed alcohol conversion of 95.6% at 93.7% selectivity to hexanal.

Example XIII

The example is similar to V but the magnesium nitrate, the N-bromosuccinimide, part of the acetic acid and the hexanol-1 were heated in argon, the AA-TEMPO solution in acetic acid was injected next, followed by pressurizing with oxygen.

0.124 of $Mg(NO_3)_2 \cdot 6H_2O$ (0.48 mmol) and 0.098 g N-bromosuccinimide (0.55 mmol) and 8 ml of hexanol-1 (64 mmol) were dissolved in 3 ml of glacial acetic acid and the resulting solution was charged into the reaction flask. The solution was purged with argon and then heated to 46° C. When the temperature reached the target value, 0.1045 g AA-TEMPO (0.48 mmol), dissolved in 1 ml acetic acid were injected into the reactor and after two minutes equilibration time, the argon was replaced for oxygen and the reactor pressurized to 1 bar (15 psi). The recorded oxygen uptake rate was 0.242 mmol $O_2$/min and the GC analysis of the reaction solution after 200 min showed alcohol conversion of 97.5% at 92.6% selectivity to hexanal.

Example XIV

The example is similar to V but the magnesium nitrate, the N-bromosuccinimide, part of the acetic acid and the hexanol-1 were heated in argon, the argon was replaced for oxygen followed the injection of the AA-TEMPO solution.

0.124 of $Mg(NO_3)_2 \cdot 6H_2O$ (0.48 mmol) and 0.098 g N-bromosuccinimide (0.55 mmol) and 8 ml of hexanol-1 (64 mmol) were dissolved in 3 ml of glacial acetic acid and the resulting solution was charged into the reaction flask. The solution was purged with argon and then heated to 46° C. When the temperature reached the target value, the argon was replaced for oxygen followed by addition of 0.1045 g AA-TEMPO, dissolved in 1 ml acetic acid. The recorded oxygen uptake rate was 0.256 mmol $O_2$/min and the GC analysis of the reaction solution after 200 min showed alcohol conversion of 96.4% at 92.6% selectivity to hexanal.

The following Examples XVII–XVII are same as Example V but the oxygen atmosphere was replaced with $N_2$—$O_2$ make up gas at 5.17 bar (75 psi).

Example XV

In this Example the $N_2/O_2$ Ratio was as 30:45

0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The flask was sealed and attached to the gas delivering volumetric unit. The catalyst solution was purged with oxygen at least three times and then heated to 48° C. while stirring. When the temperature reached the target value, the required amount of hexanol-1 (64 mmol) was injected into the reactor, using a gas tight syringe. The flask was then pressurized first with $N_2$ to 2.07 bar (30 psi) and then connected to the volumetric manifold set at oxygen delivery pressure of 5.17 bar (75 psi). The recorded oxygen uptake rate as calculated from the oxygen uptake curve was 0.260 mmol $O_2$/min and the GC analysis of the reaction solution after 140 min showed alcohol conversion of 95.3% at 95.2% selectivity to hexanal. The oxygen uptake curve for this example is shown in FIG. 2, plot 1.

Example XVI

In this Example the $N_2:O_2$ Ratio was as 60:15

0.1045 g AA-TEMPO (0.48 mmol), 0.124 g of $Mg(NO_3)_2 \cdot 6H_2O$ (0.48 mmol) and 0.098 g N-bromosuccinimide (0.55 mmol) were dissolved in 4 ml of glacial acetic acid and the resulting solution was charged into the reaction flask. The flask was sealed and attached to the gas delivering volumetric unit. The catalyst solution was purged with oxygen at least three times and then heated to 48° C. while stirring. When the temperature reached the target value, the required amount of hexanol-1 (64 mmol) was injected into the reactor, using a gas tight syringe. The flask was then pressurized first with $N_2$ to 4.14 bar (60 psi) and then connected to the volumetric manifold set at oxygen delivery pressure of 5.17 bar (75 psi). The recorded oxygen uptake rate as calculated from the oxygen uptake curve was 0.170 mmol $O_2$/min and the GC analysis of the reaction solution after 240 min showed alcohol conversion of 96.7% at 93.7% selectivity to hexanal. The oxygen uptake curve for this example is shown in FIG. 2, plot 2.

The following Examples XVII–XVIII are same as Example V but the reaction scale was 800 mmol with $N_2$—$O_2$ make up gas at 13.79 bar (200 psi) and 6.9 bar (100 psi). The oxidations were carried out in a Parr autoclave.

Example XVII 1.31 g AA-TEMPO (6.0 mmol), 1.55 g of $Mg(NO_3)_2 \cdot 6H_2O$ (6.0 mmol) and 1.23 g N-bromosuccinimide (6.9 mmol) were dissolved in 50 ml of glacial acetic acid and the resulting solution was charged into a high pressure stainless steal reaction flask. The flask was sealed and attached to the high pressure gas delivering volumetric unit. The catalyst solution was purged with oxygen at least three times and then heated to 46° C. while stirring. When the temperature reached the target value, 100 ml hexanol-1 (800 mmol) were injected into the reactor, using a gas tight syringe. The flask was then pressurized first with nitrogen to 11.03 bar (160 psi) and then connected to the volumetric manifold set at oxygen delivery pressure of 13.79 bar (200 psi). The recorded oxygen uptake rate as calculated from the oxygen uptake curve was 2.72 mmol $O_2$/min and the GC analysis of the reaction solution after 200 min showed alcohol conversion of 98.0% at 93.1% selectivity to hexanal.

Example XVIII 1.31 g AA-TEMPO (6.0 mmol), 1.55 g of $Mg(NO_3)_2 \cdot 6H_2O$ (6.0 mmol) and 1.23 g N-bromosuccinimide (6.9 mmol) were dissolved in 50 ml of glacial acetic acid and the resulting solution was charged into a high pressure stainless steal reaction flask. The flask was sealed and attached to the high pressure gas delivering volumetric unit. The catalyst solution was purged with oxygen at least three times and then heated to 46° C. while stirring. When the temperature reached the target value, 100 ml hexanol-1 (800 mmol) were injected into the reactor, using a gas tight syringe. The flask was then pressurized first with nitrogen to 5.52 bar (80 psi) and then connected to the volumetric manifold set at oxygen delivery pressure of 6.9 bar (100 psi). The recorded oxygen uptake rate as calculated from the oxygen uptake curve was 2.05 mmol $O_2$/min and the GC analysis of the reaction solution after 300 min showed alcohol conversion of 94.9% at 94.4% selectivity to hexanal.

All patents and publications mentioned above are incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A process for oxidation of an alcohol, comprising:
   reacting a primary or secondary alcohol with an oxygen-containing gas in the presence of a catalyst composition comprising
   (i) a stable free nitroxyl radical derivative,
   (ii) a nitrate source,
   (iii) a bromide source, and
   (iiii) a carboxylic acid;
   thereby obtaining an aldehyde or a ketone.

2. The process of claim 1, wherein said stable free nitroxyl radical derivative is represented by formulae (I) or (II)

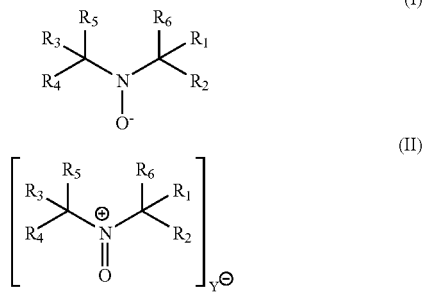

wherein
$R^1$, $R^2$, $R^3$, $R^4$, $R^5$, and $R^6$ are simultaneously or independently of each other $(C_1-C_{10})$-alkyl, $(C_1-C_{10})$-alkenyl, $(C_1-C_{10})$-alkoxy, $(C_6-C_{18})$-aryl, $(C_7-C_{19})$-aralkyl, $(C_6-C_{18})$-aryl-$(C_1-C_8)$-alkyl or $(C_3-C_{18})$-heteroaryl;

$R^5$ and $R^6$ may be bonded together via a $(C_1-C_4)$-alkyl chain, which may be saturated or unsaturated, unsubstituted or substituted by one or more $R^1$, $C_1-C_8$-amido, halogen, oxy, hydroxyl, amino, alkylamino, dialkylamino, arylamino, diarylamino, alkylcarbonyloxy, arylcarbonyloxy, alkylcarbonylamino or arylcarbonylamino; and $Y^-$ is an anion.

3. The process of claim 1, wherein said alcohol is selected from the group consisting of methanol, ethanol, propyl alcohol, butyl alcohol, pentanol, 2-methyl-1-butanol, 3-methyl-1-butanol, neopentyl alcohol, hexanol, 2-methyl-1-pentanol, neohexyl alcohol, heptanol, octanol, 2-ethyl-1-hexanol, nonyl alcohol, decyl alcohol, lauryl alcohol, dodecyl alcohol, eicosyl alcohol, unsaturated alcohols, aromatic alcohols and mixtures thereof.

4. The process of claim 1, wherein said stable free nitroxyl radical is selected from the group consisting of 2,2,6,6-tetramethylpiperidine-1-oxyl, 4-hydroxy-2,2,6,6-tetramethylpiperdine-1-oxyl, 4-methoxy-2,2,6,6-tetramethylpiperidine-1-oxyl, 4-oxo-2,2,6,6-tetramethylpiperidine-1-oxyl, 4-amino-2,2,6,6-tetramethylpiperidine-1-oxyl, 4-acetamido-2,2,6,6-tetramethylpiperidine-1-oxyl, 4-benzoyloxy-2,2,6,6-tetramethylpiperidine-1-oxyl, 3,6-dihydro-2,2,6,6-tetramethyl-1 (2H)-pyridinyl-oxyl, bis(2,2,6,6-tetramethyl-piperidine-1-oxyl-4-yl) sebacate, 4-acetamino-2.2,6,6-tetramethylpiperidine-1-oxyl, N,N-dimethylamino-2.2,6,6-tetramethyl-piperidine-1-oxyl, and mixtures thereof.

5. The process of claim 1, wherein the stable free nitroxyl radical derivative is present in an amount of from about 0.001–10 mol %, based on the amount of said alcohol.

6. The process of claim 5, wherein the stable free nitroxyl radical derivative is present in an amount of from about 0.01–2 mol %, based on the amount of said alcohol.

7. The process of claim 1, wherein the nitrate source is selected from the group consisting of an alkali nitrate, an alkaline-earth nitrate, ammonium nitrate, alkyl ammonium nitrate, nitric acid and mixtures thereof.

8. The process of claim 1, wherein the nitrate source is magnesium nitrate.

9. The process of claim 1, wherein the nitrate source is present in an amount of from about 0.01–10 mol %, based on the amount of said alcohol.

10. The process of claim 1, wherein the nitrate source is present in an amount of from about 0.1–2 mol %, based on the amount of said alcohol.

11. The process of claim 1, wherein the bromide source is selected from the group consisting of N-bromosuccinimide, N-bromophthalimide, tetrabutylammonium bromide, $NH_4Br$, an alkali bromide, an alkali-earth bromide and mixtures thereof.

12. The process of claim 1, wherein the bromide source is N-bromosuccinimide.

13. The process of claim 1, wherein the bromide source is present in an amount of from 0.01–10 mol %, based on the amount of said alcohol.

14. The process of claim 1, wherein the bromide source is present in an amount of from about 0.1–2 mol %, based on the amount of said alcohol.

15. The process of claim 1, wherein the oxygen-containing gas is selected from the group consisting of i) pure oxygen, ii) air, iii) a mixture of oxygen and an inert gas, and iv) mixtures thereof.

16. The process of claim 1, wherein the carboxylic acid is acetic acid, propionic acid, a carboxylic acid that forms a homogeneous reaction mixture and mixtures thereof.

17. The process of claim 1, wherein the carboxylic acid is acetic acid.

18. The process of claim 1, which proceeds in the presence of at least one solvent in the alcohol solution, said solvent being selected from the group consisting of acetonitrile, tetrahydrofuran, ethyl acetate, acetone, diethyl ether, methyl tert-butyl ether and mixtures thereof.

19. The process of claim 18, wherein said solvent is present in an amount of from >0 vol. % to about 70 vol. % based on the volume of said alcohol.

20. The process of claim 1, wherein the oxidation is carried out in absence of a solvent.

21. The process of claim 1, which proceeds at a reaction temperature of from 0 to 100° C.

22. The process of claim 21, which proceeds at a reaction temperature of from 20 to 80° C.

23. The process of claim 1, which proceeds at a reaction pressure of from 0.1 to 70 bar.

24. The process of claim 1, which proceeds at an oxygen partial pressure of from 0.1 to 10 bar.

25. The process of claim 1, further comprising
   purification of said aldehyde or ketone by use of a purification method selected from the group consisting of distillation, fractional distillation, crystallization, a reaction with sodium metabisulphite and combinations thereof.

26. The process of claim 1, which proceeds without the presence of a transition metal.

27. The process of claim 1, wherein said stable free nitroxyl radical derivative is represented by formulae (I) or (II)

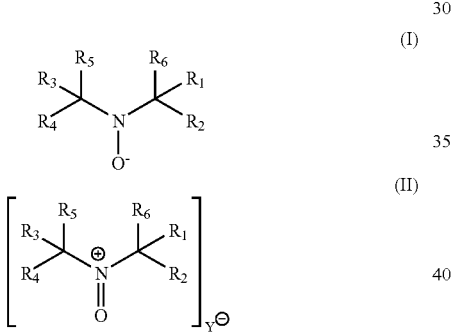

wherein
   $R^1$, $R^2$, $R^3$, $R^4$, $R^5$, and $R^6$ are simultaneously or independently of each other $(C_1-C_{10})$-alkyl, $(C_1-C_{10})$-alkenyl, $(C_1-C_{10})$-alkoxy, $(C_6-C_{18})$-aryl, $(C_7-C_{19})$-aralkyl, $(C_6-C_{18})$-aryl-$(C_1-C_8)$-alkyl or $(C_3-C_{18})$-heteroaryl;
   $R^5$ and $R^6$ may be bonded together via a $(C_1-C_4)$-alkyl chain, which may be saturated or unsaturated, unsubstituted or substituted by one or more $R^1$, $C_1-C_8$-amido, halogen, oxy, hydroxy, amino, alkylamino, dialkylamino, arylamino, diarylamino, alkylcarbonyloxy, arylcarbonyloxy, alkylcarbonylamino or arylcarbonylamino;
   $Y^-$ is an anion; and
   wherein at least one of said nitroxyl radical derivative of formulae (I) or (II) or a mixture thereof are a substituent of a macromolecule, an oligomeric structure or a polymeric structure.

28. The process of claim 1, wherein said stable free nitroxyl radical derivative is represented by formulae (I) or (II)

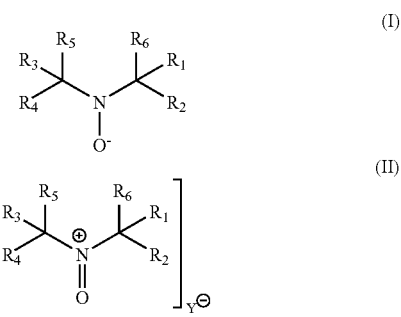

wherein
   $R^1$, $R^2$, $R^3$, $R^4$, $R^5$, and $R^6$ are simultaneously or independently of each other $(C_1-C_{10})$-alkyl, $(C_1-C_{10})$-alkenyl, $(C_1-C_{10})$-alkoxy, $(C_6-C_{18})$-aryl, $(C_7-C_{19})$-aralkyl, $(C_6-C_{18})$-aryl-$(C_1-C_8)$-alkyl or $(C_3-C_{18})$-heteroaryl;
   $R^5$ and $R^6$ may be bonded together via a $(C_1-C_4)$-alkyl chain, which may be saturated or unsaturated, unsubstituted or substituted by one or more $R^1$, $C_1-C_8$-amido, halogen, oxy, hydroxy, amino, alkylamino, dialkylamino, arylamino, diarylamino, alkylcarbonyloxy, arylcarbonyloxy, alkylcarbonylamino or arylcarbonylamino;
   $Y^-$ is an anion; and
   wherein at least one of said nitroxyl radical derivative of formulae (I) or (II) or a mixture thereof are present on a solid support.

29. The process of claim 1, wherein said alcohol is selected from the group consisting of allyl alcohol, crotyl alcohol, propargyl alcohol and mixtures thereof.

30. The process of claim 1, wherein said alcohol is selected from the group consisting of benzyl alcohol, phenyl ethanol, phenyl propanol and mixtures thereof.

* * * * *